United States Patent [19]

Yaegashi et al.

[11] 4,140,611
[45] Feb. 20, 1979

[54] OXYGEN SENSOR

[75] Inventors: Takehisa Yaegashi, Mishima; Shinichi Sugiyama; Sadayoshi Wada, both of Susono, all of Japan

[73] Assignee: Toyota Jidosha Kogyo Kabushiki Kaisha, Toyota, Japan

[21] Appl. No.: 855,616

[22] Filed: Nov. 29, 1977

[30] Foreign Application Priority Data

Jul. 25, 1977 [JP] Japan .................. 52-98288[U]

[51] Int. Cl.² ............................................. G01N 27/46
[52] U.S. Cl. .................................. 204/195 S; 204/1 T; 123/119 E
[58] Field of Search ............................ 204/15, 195 S; 123/119 E; 73/23, 421.5 R

[56] References Cited

U.S. PATENT DOCUMENTS

| 3,835,012 | 9/1974 | Hemak | 204/195 S |
| 3,843,038 | 2/1976 | Sandler | 204/15 |
| 3,977,830 | 8/1976 | Topol | 204/195 S |

FOREIGN PATENT DOCUMENTS 1511066  12/1967  France ........................ 204/195 S Primary Examiner—T. Tung
Attorney, Agent, or Firm—Stevens, Davis, Miller & Mosher

[57] ABSTRACT

An oxygen sensor which comprising: a case having an inlet means and an outlet means through which gas passes. A sensor element is installed within the case, and an oxidation catalyzer is arranged upstream of said sensor element within said case. The inlet means or oxidation catalyzer is arranged so that a part of the gas which is introduced through the inlet means into the case flows without passing through the oxidation catalyzer while the other part of said gas passes through the oxidation catalyzer.

3 Claims, 6 Drawing Figures

OXYGEN SENSOR

BACKGROUND OF THE INVENTION

The present invention relates to an oxygen sensor which detects oxygen concentration in the exhaust gas of an internal combustion engine.

A three-way catalyzer is known as one of the effective emission control devices in internal combustion engines. In the three-way catalyzer, HC (hydrocarbon) and CO (carbon monoxide) are oxidized so as to be converted into water and carbon dioxide, and simultaneously, $NO_x$ (nitrogen oxides) is deoxidized so as to be converted into nitrogen gas. In such a three-way catalyzer, in order to achieve an effective catalytic reaction in the catalyzer, the air/fuel ratio of the components in the exhaust gas must be maintained approximately constant at the stoichiometric air/fuel ratio. In order to achieve a precise control of the exhaust gas so that the stoichiometric ratio is maintained, the oxygen concentration in the exhaust gas is detected by an oxygen sensor and, in response to the output signal of the sensor, auxiliary air is supplied to the exhaust gas. Such an oxygen sensor is called an $O_2$ sensor or a $\lambda$ sensor.

The sensor element of the oxygen sensor consists of a sintered zirconium dioxide tube closed at one end. The inside and outside surfaces of the tube are coated with a thin layer of platinum. If there are different partial pressures of oxygen on both sides of the tube, electromotive force is generated between the platinum surfaces. The electromotive force steeply changes at the stoichiometric point as shown in the attached FIG. 6 by a solid line "Y". Therefore, the output signal of the sensor element can indicate whether the air/fuel ratio of the gas is richer or leaner than the stoichiometric ratio. Then, auxiliary air is supplied in response to the output signal of the sensor element.

However, in the conventioned sensor element, there is a tendency for the changing point of the electromotive force to be shifted to the lean side, as shown in FIG. 6 by a dot-dash line "Z", due to an oxidizing catalytic characteristic of the platinum coated on the tube surfaces. Such a sensor element indicates the stoichiometric point when the gas is leaner than the stoichiometric ratio. This results in the air/fuel ratio, which is controlled by the sensor element, being shifted to the lean side of the stoichiometric ratio and the three-way catalyzer does not work satisfactorily.

In order to obviate the above drawback, an improved oxygen sensor has already been utilized. This improved sensor comprises a case having an inlet means and an outlet means through which gas passes, a sensor element installed within said case, and an oxidation catalyzer arranged upstream of said sensor element within said case. However, in such an oxygen sensor, the changing point of the electromotive force of the sensor is shifted to the rich side, as shown in FIG. 6 by a dotted line "X", due to the characteristic of the oxidation catalyzer. Such an oxygen sensor indicates the stoichiometric point when the gas is richer than stoichiometric ratio. This results in the air/fuel ratio, which is controlled by the sensor, being shifted to the rich side of the stoichiometric ratio and the three-way catalyzer does not work satisfactorily. In this case, if the oxidation catalyzer has an extremely high catalytic ability which oxidizes over 95% of $H_2$ and HC in the gas simultaneously, the changing point of the electromotive force of the sensor is not shifted to the rich side. However, such a high catalytic ability can not be maintained over a long period of time and, in addition, such a catalyzer is expensive. Further, a large ammount of catalyzer is needed and the surface of the catalyzer must be widened so as to fully contact the gas, which results is increased resistance against the gas flow.

SUMMARY OF THE INVENTION

It is an object of the present invention to provide an oxygen sensor in which the above drawbacks are obviated and the changing point of the electromotive force of the sensor element is reliably and easily maintained at the stoichiometric point. Such an oxygen sensor comprises: a case having an inlet means and an outlet means through which gas passes; a sensor element installed within said case, and; an oxidation catalyzer arranged upstream of said sensor element within said case, wherein said inlet means or said oxidation catalyzer is arranged so that a part of the gas which is introduced through said inlet means into said case flows without passing through said oxidation catalyzer while the other part of said gas passes through said oxidation catalyzer.

BRIEF DESCRIPTION OF THE DRAWINGS

The present invention will now be further described with reference to the accompanying drawings, in which.

DETAILED DESCRIPTION OF THE PREFERRED EMBODIMENTS OF THE INVENTION

Figures 1, 2:
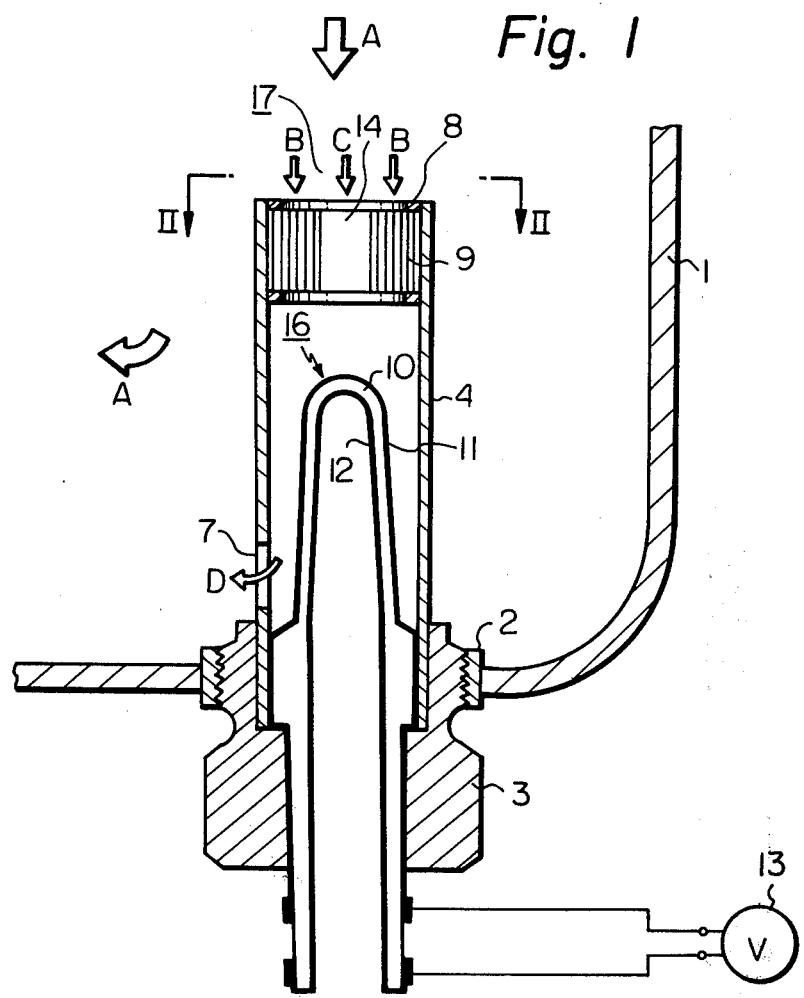
FIG. 1 is a sectional view of a first embodiment of the invention.
FIG. 2 is a view from the direction of arrows II—II in FIG. 1.

In FIG. 1, exhaust gas flows in the direction of arrow A within an exhaust pipe 1. The illustrated oxygen sensor comprises: a case 4 having an inlet means 17 and an outlet means 7; a sensor element 16 installed within the case 4, and; an oxidation catalyzer 9 arranged upstream of the sensor element 16 within the case 4. The sensor element 16 consists of a sintered zirconium dioxide tube 10 closed at one end. An inside surface 12 and an outside surface 11 of the tube 10 are coated with a thin layer of platinum. The case 4 is secured to the exhaust pipe 1 by a bolt 3 via a sealing member 2. An electromotive force meter 13 is connected between the inside and outside platinum surfaces 12 and 11. A honeycomb type oxidation catalyzer 9 is installed at the top end of the case 4 between supports 8 and 8. The oxidation catalyzer 9 has a center through hole 14 (see FIG. 2).

Figure 6:
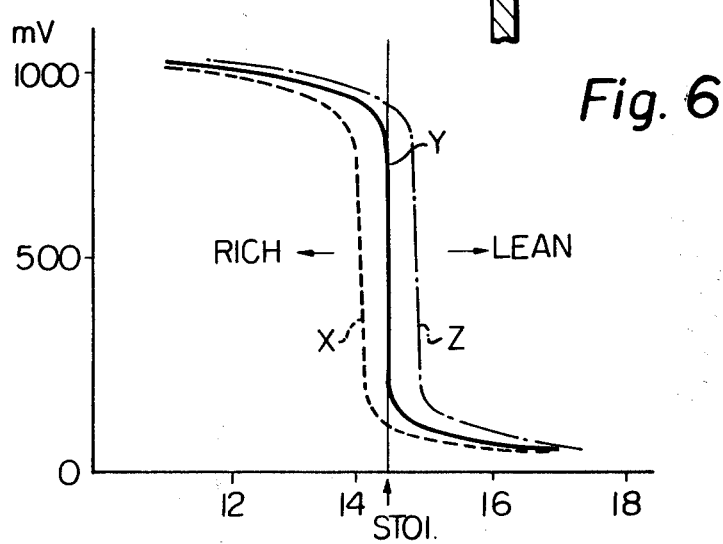
FIG. 6 shows graphs of the electromotive force of the sensor element with respect to the air/fuel ratio.

A part of the exhaust gas which is introduced through the inlet means 17 into the case 4 passes through the hole 14 without passing through the catalyzer as is indicated by an arrow C, while the other part of the exhaust gas passes through the oxidation catalyzer 9 as is indicated by arrows B. The gas flows B and C are mixed within the case 4. The mixed gas reaches the sensor element 16 and then flows out of the case 4 through the outlet 7 as indicated by an arrow D. The electromotive force meter detects the electromotive force which corresponds to the oxygen concentration in the exhaust gas. The gas which passes through the oxidation catalyzer 9, indicated by the arrow B, shifts the changing point of the electromotive force of the sensor element 16 to the rich side as shown by the dotted line "X" in FIG. 6. On the other hand, the gas which passes through the hole 14, indicated by the arrow C, shifts the changing point of the electromotive force of the sensor element 16 to the lean side as shown by the dot-dash line "Z" in FIG. 6. Accordingly, the electromotive force always steeply changes at the stoichiometric point, as shown by the solid line "Y", in the mixed gas of the gas flow B and the gas flow C.

Thus, in the oxygen sensor according to the invention, the changing point of the electromotive force is easily and reliably maintained at the stoichiometric point using a normal oxidation catalyzer which oxidizes over 40% of HC, CO and $H_2$ in the gas instead of using an expensive oxidation catalyzer of high quality which oxidizes over 95% of HC, CO and $H_2$ in the gas. Accordingly, in the emission control system comprising a three-way converter, the auxiliary air can be reliably controlled so that the exhaust gas is always maintained at the stoichiometric ratio and, thus, the three-way converter effectively acts upon $NO_x$, CO and HC emissions simultaneously.

Figure 3:
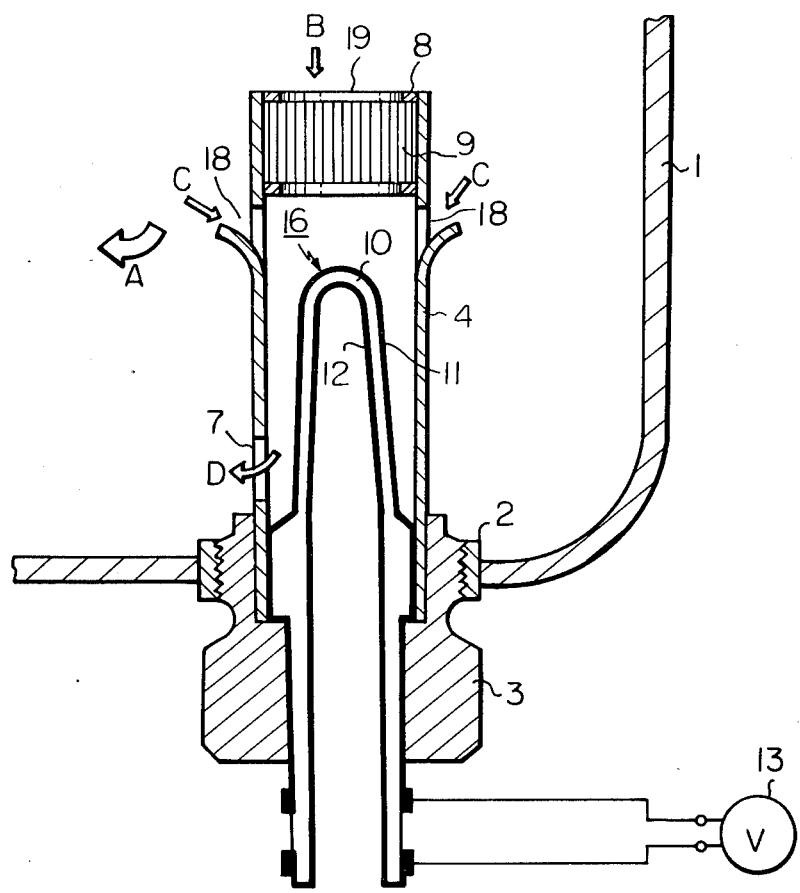
FIG. 3 is a sectional view of a second embodiment of the invention.
Figure 4:
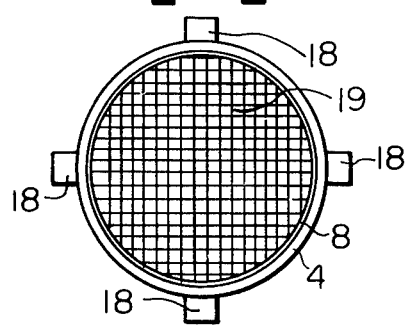
FIG. 4 is a view from the direction of arrows IV—IV in FIG. 3.

Another embodiment of the invention is illustrated in FIG. 3. In this embodiment, the case 4 has a first inlet 19 at its top end and second inlets 18 on its side wall. The gas introduced from the first inlet 19 passes through the oxidation catalyzer 9, while the gas introduced from the second inlets 18 reaches the sensor element 16 without passing through the catalyzer 9. In this case, the oxidation catalyzer 9 covers the entire area of the inlet 19 as shown in FIG. 4. The construction and the function of the second embodiment, except as described above, are substantially the same as those of the first embodiment.

Figure 5:
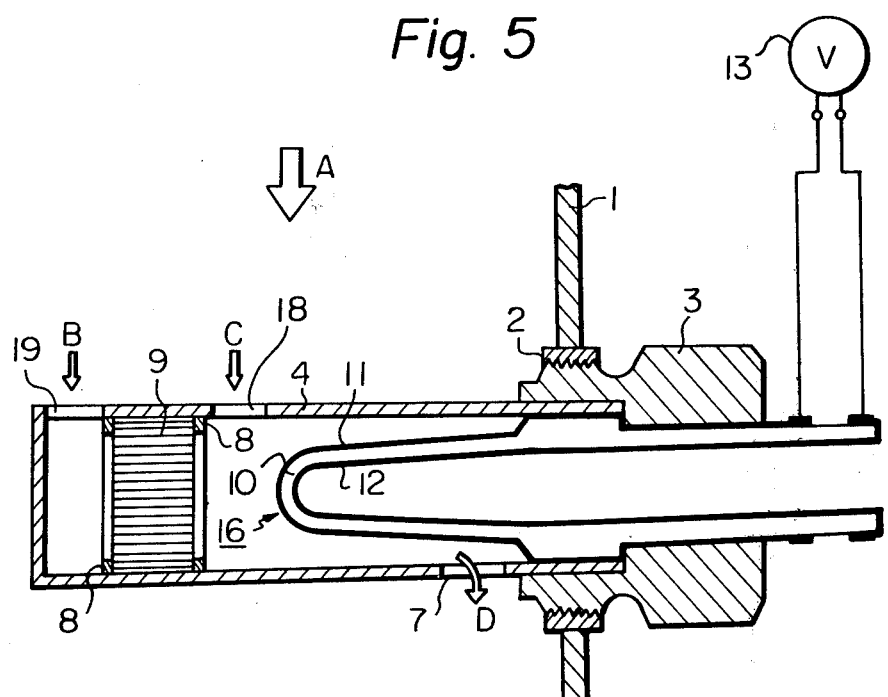
FIG. 5 is a sectional view of a third embodiment of the present invention.

A further embodiment of the invention is illustrated in FIG. 5. The case 4 is installed perpendicular to the exhaust gas flow A. The case 4 has a first inlet 19 and a second inlet 18. The construction and the function of the third embodiment are substantially the same as those of the second embodiment.

In the above embodiments, the ratio of the gas which flows without passing through the oxidation catalyzer to the entire gas introduced into the case is 20-70% and this ratio can be desirably adjustable so as to match the ability of the oxidation catalyzer.

The present invention is not limited to the above described embodiments, but can be modified within the scope of the appended claims.

What is claimed is:

1. An oxygen sensor for sensing the concentration of oxygen gas within the exhaust gas produced by an internal combustion engine comprising:
   a case having an inlet means and an outlet means through which gas passes;
   a solid electrolyte oxygen sensor having two surfaces installed within said case; and,
   an oxidation catalyzer spaced from and arranged upstream of said solid electrolyte oxygen sensor within said case;
   wherein said inlet means and said oxidation catalyzer are arranged so that a part of the gas which is introduced through said inlet means into said case flows without passing through said oxidation catalyzer, while the other part of said gas passes through said oxidation catalyzer and so that the mixed gas of said two parts contacts one of said surfaces of said solid electrolyte oxygen sensor.

2. An oxygen sensor according to claim 1, wherein said oxidation catalyzer has a through hole through which said first-mentioned part of said gas passes without contacting the catalyzer.

3. An oxygen sensor according to claim 1, wherein said inlet means comprises a first inlet means and a second inlet means, said first inlet means being arranged upstream of said oxidation catalyzer, while said second inlet means being arranged downstream of said oxidation catalyzer.

* * * * *